United States Patent [19]

Henderson et al.

[11] 4,274,861

[45] Jun. 23, 1981

[54] PLANT GROWTH STIMULANT

[75] Inventors: Alan Henderson, Glendora; L. E. Chamblee, Greenwood, both of Miss.

[73] Assignee: Inter Chem, Ltd., Greenwood, Miss.

[21] Appl. No.: 33,672

[22] Filed: Apr. 26, 1979

Related U.S. Application Data

[63] Continuation-in-part of Ser. No. 919,483, Jun. 27, 1978, abandoned, which is a continuation of Ser. No. 737,484, Nov. 1, 1976, abandoned.

[51] Int. Cl.³ .................. A01N 37/38; A01N 31/02
[52] U.S. Cl. ................................ 71/117; 71/122
[58] Field of Search ............... 71/117, 122, DIG. 1

[56] References Cited

U.S. PATENT DOCUMENTS

| | | | |
|---|---|---|---|
| 2,390,941 | 12/1945 | Jones | 71/117 |
| 2,510,839 | 6/1950 | Schmidl | 71/117 |
| 2,558,762 | 7/1951 | Kohr, Jr. et al. | 71/117 |
| 3,472,647 | 10/1969 | Miller | 71/122 |
| 3,554,732 | 1/1971 | Priola | 71/117 |
| 3,630,717 | 12/1971 | Miller | 71/122 |
| 3,711,273 | 1/1973 | Mitchell | 71/120 |
| 3,737,298 | 6/1973 | Fielding | 71/77 |
| 3,989,500 | 11/1976 | Ku | 71/99 |

OTHER PUBLICATIONS

Wort, I, "Responses of Plants to Sublethal Concentrations, etc.," (1964) Physiol. & Biochem. of Herbicides, pp. 335–342 (1964).
Johnson et al., "Interaction of 2,3,5-TIBA etc.," (1974) CROP Sci. 14, pp. 381–384 (1974).
Miller et al., "Effects of Stimulator and Inhibitory etc.," (1962) CROP Sci. 2, pp. 111–116 (1962).
Wort II, "Effects of 2,4-D Nutrient Dusts, etc.," (1966) AGRON. J. 58, pp. 27–29 (1966).

*Primary Examiner*—Glennon H. Hollrah
*Attorney, Agent, or Firm*—Pennie & Edmonds

[57] ABSTRACT

A composition and its method of application for stimulating plant growth and enhancing fruit production in leguminous plants, for example, in soybeans. The composition employs a lower aliphatic alcohol such as methanol in combination with 2,4-D Herbicide, a surfactant, and a suitable adherent. The composition is applied and maintained on the plants during the flowering stage of the plant.

13 Claims, No Drawings

PLANT GROWTH STIMULANT

CROSS-REFERENCE TO RELATED APPLICATIONS

This application is a continuation-in-part of parent application Ser. No. 919,483, filed June 27, 1978, now abandoned which in turn is a continuation of parent application Ser. No. 737,484, filed Nov. 1, 1976, now abandoned.

BACKGROUND OF THE INVENTION

1. Field of the Invention

The present invention relates to compositions for stimulating plant growth, and more particularly, the present invention relates to a composition and its method of application to leguminous plants to thereby increase the yield amount of fruit produced from the plants.

2. General Background and Prior Art

It is known in the art to use various agricultural growth promoters. In addition to the chemical composition of the particular growth stimulant which may be emloyed to increase the yield of a given plant or crop, it is also important that the method of application (including the time period in which the chemical is applied in a certain stage of the plant growth cycle), be carefully controlled. In fact, interaction of the particular growth stimulant composition, its ability to adhere to the plant are all vital to an increase in fruit yield from a given crop.

Several methods and compositions for stimulating plant growth have been patented. The following table lists some of these prior art patents:

| U.S. PAT. NO. | INVENTORS | ISSUE DATE |
|---|---|---|
| 2,842,051 | P. W. Brian et al | 7/8/56 |
| 3,004,845 | R. J. LaPierre | 10/17/61 |
| 3,102,017 | R. A. Shurter, Jr, | 8/27/63 |
| 3,199,971 | G. Shimazaki | 8/10/65 |
| 3,210,173 | T. M. Mozell | 10/5/76 |
| 3,472,647 | G. T. Miller | 10/14/69 |
| 3,630,717 | G. T. Miller | 12/28/71 |
| 3,764,294 | G. T. Miller | 10/9/73 |
| 3,915,686 | G. T. Miller | 10/28/75 |

SUMMARY OF THE INVENTION

The present invention provides a composition for stimulating leguminous plant growth and the corresponding enhancement of fruit yield and a method of applying the composition to the plant at a certain time stage of the plant's growth cycle. The composition employs a standard alcohol, such as methanol, a particular herbicide commonly known as 2,4-D Herbicide, a surfactant, and a suitable adherent agent, such as conventional diesel fuel. The adhering agent is utilized to maintain contact between the growth stimulating composition and the plant during stages of the plant growth cycle at which operation of the composition has greatest effect on ultimate fruit production. Water can be added as necessary to dilute the solutions to desired concentrations. The time of application is during the flowering period.

DESCRIPTION OF THE PREFERRED EMBODIMENTS

The present application is concerned with a composition and its method of application for stimulating leguminous fruit yield production or leguminous plant growth by applying and maintaining the composition on the plant during a certain time, for example, during the flowering period of the plant growth cycle. It is understood that the term "fruit" is meant the product of the plant growth, the usable or eatable productive body portion of the plant. It should also be understood that the application of the composition can be to the leguminous plant itself or to the soil in which it is growing or the surroundings in which the plant is placed.

The method of application of the composition can be by spraying such as, for example, with a crop duster.

The composition includes an alcohol and can be a standard alcohol such as methanol, ethanol, butanol, propanol and like lower aliphatic alcohols although methanol is preferred. Along with the alcohol is used a relatively minute amount of standard 2,4-D Herbicide. Standard 2,4-D Herbicide is an alkanolamine salt of ethanol and isopropanol series of 2,4-dichlorophenoxyacetic acid, 59.7 weight % and inert 40.3 weight %. It will be understood that, in contrast to the foregoing, active 2,4-D Herbicide contains substantially no inert material. The composition further includes a surfactant solution and a suitable adhering agent. Any of the many well known surfactants can be used such as, for example, "Tween 20" manufactured by the Atlas Power Co., as well as any of the many well known adhering agents such as, for example, standard diesel fuel. Additionally, a certain amount of water can be added to dilute the solution to the desired concentratation.

It has been found that the amount of 2,4-D Herbicide that may be incorporated in the composition that is to be applied to the plant may range from about 100 ppm by weight to about 200 ppm by weight of standard 2,4-D Herbicide product—this includes about 40.3% by weight of inert material such that the range of active 2,4-D Herbicide is from about 60 to about 120 ppm by weight—while the alcohol may range from about 10,000 ppm by weight to about 80,000 ppm by weight. The foregoing 2,4-D Herbicide and alcohol ranges have been found to be particularly suitable for application under field conditions. The preferred composition that is to be applied to the plants may preferably contain about 167 ppm by weight standard 2,4-D Herbicide—about 100 ppm by weight active 2,4-D Herbicide—and about 44,000 ppm by weight alcohol.

It has also been found that the amount of 2,4-D Herbicide that may be incorporated in the composition that is to be applied to the plants may range from about 10 ppm by weight to below 30 ppm by weight of standard 2,4-D Herbicide product—this again includes about 40.3% by weight of inert material such that the range of active 2,4-D Herbicide is from about 6 ppm by weight to below 18 ppm by weight—while the amount of alcohol may range from about 10 ppm by weight to about 20,000 ppm by weight. The foregoing 2,4-D Herbicide and alcohol ranges have been found to be particularly suitable for application to leguminous plants under greenhouse conditions.

It is theorized that the difference in effectiveness between greenhouse and field applications of the respective amounts of 2,4-D Herbicide and alcohol may be due to the inherent difference of the plants when grown under the different conditions.

With respect to the surfactant and the adhering agent of the claimed composition, the amounts of these constituents are not at all critical; the surfactant and adhering agents may each be used in the formulation that will be applied to the plants in amounts from about 10 to about 10,000 ppm by weight. The preferred formulation contains about 400 ppm by weight of surfactant and about 500 ppm by weight of adhering agent when the standard 2,4-D Herbicide is in the range of 10-30 ppm by weight and about 4000 ppm by weight of surfactant and about 5000 ppm by weight of adhering agent when the standard 2,4-D Herbicide is in the range of 100-200 ppm by weight.

It has been found that improved results are obtained when the composition of this invention is applied in an amount of at least about 0.3 gallons/acre although the exact rate of application can easily be determined. It should be noted that too great an amount of 2,4-D Herbicide applied to, for example, soybeans, as by the application of too high a rate of the composition, may be lethal and fumes of 2,4-D Herbicide may upset a hormone balance in cotton sometimes as much as miles away depending upon the 2,4-D Herbicide concentration. The optimum upper rate of application can, as noted, be easily determined.

The following Table lists exemplary chemical configurations for the preferred composition of the present invention. Table 1 illustrates typical specifications including (A) concentrations by weight percent without water, (B) concentrations by weight percent as retailed to applicators who would actually purchase the compositions and who would dilute it to the desired composition, and finally (C) the composition as applied to a leguminous crop, such as soybeans:

TABLE 1

| TYPICAL SPECIFICATIONS | | |
|---|---|---|
| COMPOSITION: | | |
| (A) Concentrate- By Weight % | (1) Standard test diesel fuel | .08970 |
| | (2) Undiluted methanol $CH_3OH$ | .83314 |
| | (3) Any mean surfactant | .07403 |
| | *(4) 2,4-D Herbicide | .00314 |
| (B) Retail to Applicator- By Weight % | (1) Standard test diesel fuel | .053365 |
| | (2) Undiluted methanol | .495710 |
| | (3) Any mean surfactant | .044048 |
| | (4) 2,4-D Herbicide | .001866 |
| | (5) $H_2O$ | .405009 |
| COMPOSITION: (Preferred) | | |
| (C) As applied to Soybeans- By Weight % | (1) Standard test diesel fuel | .004780 |
| | (2) Undiluted methanol | .044399 |
| | (3) Any mean surfactant | .003945 |
| | (4) 2,4-D Herbicide | .000167 |
| | (5) $H_2O$ | .946709 |

NOTE:
Allow Standard Fluxation $H_2O$ content ± .00012
*2,4-D Herbicide - alkanolamine salts of ethanol and isopropanol series of 2,4-dichlorophenoxyacetic acid 59.7 weight % inert-40.3 weight %

This invention will be described in further detail by reference to the following examples which are given only by way of illustration and not to limit the invention. Further, while the following examples are specifically directed to the application of the composition of this invention to soybeans, it should be understood that the invention is suitable for the beneficial application to any leguminous plant such as beans, peas, lentils and the like although it is preferably applied to soybeans.

EXAMPLE 1

The first experiment was conducted at Murphy Brothers Plantation in Tippo, Mississippi. The experimentation entailed a 140 acre field of soybeans. The particular of bean planted throughout the 140 acres was Dare Soybeans. The average soybean yield for the State of Mississippi is approximately 22 bushels per acre. The experimentation field of 140 acres was divided into two parts, part A being 90 acres and part B being 50 acres. For the purposes of the experiment, tract A (90 acres) was selected as the test tract and tract B (50 acres) as a control. For the purposes of the experiment, it was necessary that the tracts have uniform soil conditions throughout and uniform drainage conditions. Past history of the tracts involved indicated that only soybeans had been planted in the tract. The Dare Soybeans were planted throughout the 140 acres, the planting completed on the same data, that data being May 1.

All chemical applications made to the entire 140 acre tract were applied through the 140 acres with the exception of the composition which is the subject of the present application (referred hereafter as Formula 14-12). On July 11, the soybeans began uniform flowering. Application was made by spraying the concentration in a composition similar to that in Table 1 described as applied to soybeans. At the time of application, it was noted that the soybeans were in excellent condition having received sufficient moisture. There was some notable dynap damage, dynap being a Herbicide for cockelburs. The average height of the soybeans throughout the 140 acres at the date of application was 36 inches. The soil type in this particular case was moderate to heavy. The dates of application follow by numbers: (1) July 13, (2) July 17; (3) July 19; (4) July 23; (5) July 30. The chemical was applied with the general intention of keeping the leaves coated during the flowering period. The greater variation of time between the fourth and fifth applciations was due to the lack of moisture. Although this particular area received more moisture than most, drought stress were becoming more apparent. The first visible differences were confirmed on July 23, as follows: (1) No observable color variation between test and control; (2) Observe minor variation—leaf size and general business of plant. That, of course, refers to extraneous leafing; (3) There was a minor variation in height between test and control at this time approximately 2 inches; (4) The blooming in the test area of the field was approximately 15% on the average greater than the controlled tract B.

By the second week in August, the following effects were observed: the height differential between test tract A and control tract B was 11 inches; the height of the control area B measured 43 inches; the height of the test area measured 54 inches; the size of largest leaves in the area of test was approximately 50% larger than the acres of the control tract. There appeared to be on the average about an 80% difference in struck blooms between the test area and the control tract. Nodule fixation in the test area was running approximately 150% to 200% over the control tract. Independent laboratory tests later confirmed that the test area had 68.2% more pods by weight than the control tract.

EXAMPLE 2

A duplication of the previously described procedure was used on Ellendale Plantation at Glendora, Mississippi. The results being: (1) no substantial difference in size of plant; (2) no substantial difference in the number of extraneous leaves; (3) a minor observable difference in the size of the leaf; (4) no substantial variation in the number of nodules; and (5) between 30% and 40% increase in struck blooms.

These blooms have at this point become pods and it appears that there was retained a 30% to 40% increase in the number of pods by weight. The general interpretation of the results received from over 1,000 acres of test in the Mississippi Delta further indicated that moisture is a crucial factor in the application of the composition which is the preferred embodiment of the present application. Under more ideal conditions, it appears that one may expect a minimum of 50% increase in soybean yield.

EXAMPLE 3

A series of green house experiments were conducted whereby a total of 150 pots, each being 3 gallons in capacity and containing 2:1:1 soil: sand: peat formulation, were planted with 4 Corsoy variety soybean seeds per pot. Subsequently, the plants were thinned to 2 plants per pot and 120 of the most uniform pots were selected. The pots were each fertilized with approximately 4 grams of a 0-20-20 (nitrogen-phosphorous-potassium) commercial fertilizer. A restricted experimental design was imposed whereby the pots were arranged 6 rows wide with 20 pots per row. Each row represented 1 replication for a total of 6 replications at each formulation to be tested. The first treatment of the first replication was applied to the first plants of the first row (first replication); the first treatment of the second replication was applied to the fourth pot of the second row (second replication); the first treatment of the third replication was applied to the seventh pot of the third row (third replication), etc. A total of twenty different treatments were applied as follows:

TABLE II

| Treatment | 2,4-D Herbicide* | Methanol | Surfactant | Adherent* |
|---|---|---|---|---|
| 1 | 0 | 0 | 390 | 490 |
| 2 | 0 | 10 | " | " |
| 3 | 0 | 100 | " | " |
| 4 | 0 | 1000 | " | " |
| 5 | 1 | 10 | " | " |
| 6 | 1 | 100 | " | " |
| 7 | 1 | 1000 | " | " |
| 8 | 10 | 10 | " | " |
| 9 | 10 | 100 | " | " |
| 10 | 10 | 1000 | " | " |
| 11 | 20 | 10 | " | " |
| 12 | 20 | 100 | " | " |
| 13 | 20 | 1000 | " | " |
| 14 | 30 | 10 | " | " |
| 15 | 30 | 100 | " | " |
| 16 | 30 | 1000 | " | " |
| 17 | 40 | 10 | " | " |
| 18 | 40 | 100 | " | " |
| 19 | 40 | 1000 | " | " |
| 20 | 0 | 30,000 | " | " |

*The surfacant employed in these series of tests was Tween -"20" and the adherent was diesel fuel; the 2,4-D Herbicide compound was composed of 59.7% by weight active material and 40.3% by weight inert matter.

The above treatments, in aqueous solution, were first applied to the soybean plants shortly after the plants began to flower. The initial application of each solution was about 5 ml of solution per pot. A second application of 5 ml of solution per pot was made five days later. The plants were subsequently harvested by hand and the soybean pods (fruit) were weighed with the following results:

TABLE III

| | Weight (seed grams)/2 plants | | | | | | Total |
|---|---|---|---|---|---|---|---|
| | Replication No. | | | | | | |
| Treatment | 1 | 2 | 3 | 4 | 5 | 6 | wt/12 plants |
| 1 | 9.8 | 11.1 | 10.2 | 10.3 | 9.6 | 10.5 | 61.5 |
| 2 | 10.5 | 9.3 | 9.5 | 9.9 | 10.7 | 9.5 | 59.4 |
| 3 | 10.4 | 10.9 | 10.4 | 10.3 | 9.0 | 10.1 | 61.1 |
| 4 | 11.7 | 10.4 | 8.3 | 9.8 | 11.0 | 11.4 | 62.6 |
| 5 | 11.6 | 11.3 | 9.9 | 10.8 | 10.2 | 9.2 | 63.0 |
| 6 | 10.0 | 9.0 | 11.4 | 10.8 | 12.8 | 8.0 | 62.0 |
| 7 | .2 | 8.7 | 10.6 | 11.1 | 12.0 | 9.4 | 61.0 |
| 8 | 11.2 | 10.9 | 10.8 | 1.1 | 11.2 | 11.1 | 66.3 |
| 9 | 11.6 | 12.0 | 12.3 | 9.8 | 9.6 | 9.7 | 65.0 |
| 10 | 10.0 | 11.8 | 12.6 | 10.4 | 11.8 | 10.3 | 66.9 |
| 11 | 10.5 | 9.6 | 9.7 | 10.9 | 12.0 | 11.2 | 64.1 |
| 12 | 9.5 | 11.0 | 11.4 | 10.0 | 12.5 | 11.6 | 66.0 |
| 13 | 9.6 | 10.2 | 10.2 | 11.6 | 10.9 | 11.9 | 64.4 |
| 14 | 11.9 | 10.7 | 10.6 | 9.8 | 10.3 | 9.5 | 62.8 |
| 15 | 9.7 | 9.4 | 9.0 | 8.8 | 12.3 | 13.3 | 62.5 |
| 16 | 12.1 | 9.8 | 9.6 | 10.0 | 10.4 | 10.6 | 62.5 |
| 17 | 11.3 | 9.6 | 11.3 | 8.4 | 8.8 | 10.7 | 60.1 |
| 18 | 8.4 | 9.5 | 10.5 | 9.3 | 9.3 | 8.9 | 55.9 |
| 19 | 8.8 | 9.8 | 10.0 | 9.3 | 8.7 | 9.1 | 55.7 |
| 20 | 11.0 | 11.8 | 11.5 | 9.9 | 9.3 | 9.1 | 62.6 |

From the above Tables II and III it can be seen that significant improvement in fruit yield comes about by the use of the composition of this invention when the total 2,4-D Herbicide content of the formulation is between about 10 and 30 ppm by weight—i.e., when the 2,4-D Herbicide product contains 59.7% by weight active material and 40.3% by weight inert material which corresponds to about 6-18 ppm by weight active 2,4-D Herbicide.

EXAMPLE 4

A series of field tests were conducted whereby Solan and Harcor variety soybean seeds were planted in 30 inch rows and in 27 foot plots. A total of 168 plots were seeded comprising a total of four rows. Only two center rows were selected for purposes of this experiment. The seeds were treated with a standard herbicide and fertilized. The plots were selected for spraying according to a randomized field diagram. Each treatment was applied to different plots for each soybean seed variety planted. A total of twenty-one different treatments were applied as follows:

TABLE IV

| | Concentration (ppm by wt.) | | | |
|---|---|---|---|---|
| Treatment | 2,4-D Herbicide* | Methanol | Surfactant | Adherent |
| 1 | 0 | 0 | 406 | 625 |
| 2 | 0 | 100 | " | " |
| 3 | 0 | 1000 | " | " |
| 4 | 0 | 20,000 | " | " |
| 5 | 0 | 30,000 | " | " |
| 6 | 0 | 0 | " | " |
| 7 | .84 | 10 | " | " |
| 8 | 1.68 | 10 | " | " |
| 9 | 8.38 | 10 | " | " |
| 10 | 33.5 | 10 | " | " |
| 11 | 59.6 | 10 | " | " |
| 12 | 67.0 | 10 | " | " |
| 13 | .84 | 10 | " | " |
| 14 | 1.68 | 10 | " | " |
| 15 | 0 | 0 | " | " |
| 16 | .84 | 30,000 | " | " |
| 17 | 1.68 | 30,000 | " | " |
| 18 | 8.38 | 30,000 | " | " |
| 19 | 33.5 | 30,000 | " | " |
| 20 | 59.6 | 30,000 | " | " |

TABLE IV-continued

| Treatment | Concentration (ppm by wt.) | | | |
|---|---|---|---|---|
| | 2,4-D Herbicide* | Methanol | Surfactant | Adherent |
| 21 | 67.0 | 30,000 | " | " |

*The recited amounts of 2,4-D Herbicide contain 59.7% by weight active material and 40.3% by weight inert material.

The above treatment, in aqueous solution, were first applied to the plants shortly after the plants began to flower. The initial application of each composition was made at a rate of 0.3 gallons/acre. A second application of each composition, at the same rate, was made five days thereafter except that a second application was not made for treatment Nos. 13 and 14. The plants were subsequently mechanically harvested and the pods (fruit) were weighed with the following results:

TABLE V

| Treatment No. | Harcor (lbs) | Sum (lbs) | Solan (lbs) | Sum (lbs) | Sum For Both Varieties (lbs) | Yield-bushels/acre* |
|---|---|---|---|---|---|---|
| 1 | 11.4 | 10.0 | 21.4 | 10.0 | 9.4 | 19.4 | 40.8 | 54.9 |
| 2 | 11.5 | 10.7 | 22.2 | 10.3 | 10.3 | 20.6 | 42.8 | 57.6 |
| 3 | 11.3 | 10.6 | 21.9 | 10.7 | 10.5 | 21.2 | 43.1 | 58.0 |
| 4 | 12.1 | 10.2 | 22.3 | 10.4 | 10.2 | 20.6 | 42.9 | 57.7 |
| 5 | 11.3 | 9.6 | 20.9 | 10.7 | 11.1 | 21.8 | 42.7 | 57.4 |
| 6 | 11.8 | 12.0 | 23.8 | 10.5 | 10.5 | 21.0 | 44.8 | 60.2 |
| 7 | 11.8 | 10.5 | 22.3 | 10.2 | 8.5 | 18.7 | 41.0 | 55.1 |
| 8 | 11.0 | 10.8 | 21.8 | 9.7 | 10.6 | 20.3 | 42.1 | 56.6 |
| 9 | 10.8 | 11.2 | 22.0 | 9.9 | 10.7 | 20.6 | 42.6 | 57.3 |
| 10 | 11.6 | 10.7 | 22.3 | 10.2 | 10.6 | 20.8 | 43.1 | 58.0 |
| 11 | 11.4 | 10.7 | 22.1 | 11.0 | 10.5 | 21.5 | 43.6 | 58.6 |
| 12 | 10.7 | 11.0 | 21.7 | 11.1 | 11.0 | 22.1 | 43.8 | 58.9 |
| 13 | 12.1 | 11.8 | 23.9 | 10.3 | 9.8 | 20.1 | 44.0 | 59.2 |
| 14 | 10.5 | 10.7 | 21.2 | 10.5 | 11.0 | 21.5 | 42.7 | 57.4 |
| 15 | 11.4 | 11.9 | 23.3 | 9.9 | 10.2 | 20.1 | 43.4 | 58.4 |
| 16 | 10.8 | 11.1 | 21.9 | 10.5 | 10.1 | 20.6 | 42.5 | 57.2 |
| 17 | 11.2 | 11.7 | 22.9 | 11.0 | 10.4 | 21.4 | 44.3 | 59.6 |
| 18 | 10.6 | 10.7 | 21.3 | 10.0 | 10.8 | 20.8 | 42.1 | 56.6 |
| 19 | 11.3 | 11.0 | 22.3 | 10.7 | 10.7 | 21.4 | 43.7 | 58.8 |
| 20 | 11.2 | 10.8 | 22.0 | 10.3 | 9.7 | 20.0 | 42.0 | 56.5 |
| 21 | 12.2 | 11.3 | 23.5 | 9.7 | 10.2 | 19.9 | 43.4 | 58.4 |

*Bushel/acre yield is obtained by multiplying the sum of both varieties by 1.345 based upon each plot being 27 ft. long and 30 inches wide.

From the previous Tables IV and V it can be seen that treatments employing 2,4-D Herbicide and alcohol outside the ranges recited earlier do not bring about an improvement in yield.

EXAMPLE 5

A further field test was carried out under conditions substantially identical to those described in Example 4 except that the composition employed was the preferred composition of this invention as recited under "Composition (C)" in Table 1. This composition was applied to the soybean plants, at a rate of 0 (controls), 0.3, 0.6 and 0.9 gallons/acre, shortly after the plants began to flower, and the application was repeated in accord with a randomized field diagram for a total of four replications. A second application at the same respective rates was applied 5 days thereafter and a third application at the same respective rates was applied 3 days after that. The plants were subsequently mechanically harvested and the pods (fruit) were weighed with the following results:

TABLE VI

| Replication No. | Application Rate-Harcor | | | | Application Rate-Solan | | | |
|---|---|---|---|---|---|---|---|---|
| | 0 | .3 | .6 | .9 | 0 | .3 | .6 | .9 |
| 1 | 11.3 | 11.1 | 11.6 | 12.7 | 10.5 | 10.1 | 12.4 | 12.2 |
| 2 | 11.5 | 11.4 | 12.2 | 12.2 | 9.9 | 10.3 | 11.4 | 11.6 |
| 3 | 10.8 | 11.5 | 11.6 | 12.4 | 9.9 | 11.3 | 12.6 | 11.2 |
| 4 | 11.4 | 11.3 | 12.1 | 12.4 | 10.4 | 10.2 | 10.9 | 11.4 |
| Total lbs: | 45.0 | 45.3 | 47.5 | 49.7 | 40.7 | 41.9 | 47.3 | 46.4 |
| bushels/acre: | 60.5 | 60.9 | 63.3 | 66.3 | 54.7 | 56.3 | 63.2 | 62.4 |

From the above Table VI it can be seen that the use of the preferred composition of this invention gave good results at application rates above about 0.3 gallons/acre.

We claim:

1. A method for increasing stage of the growth cycle an aqueous composition comprising from about 60 to about 120 ppm by weight active 2,4-D Herbicide, from about 10,000 to about 80,000 ppm by weight lower aliphatic alcohol, a surfactant and an adhering agent each in amounts of from about 10 to about 10,000 ppm.

2. The method of claim 1 wherein the amount of active 2,4-D Herbicide is about 100 ppm by weight and wherein the amount of lower aliphatic alcohol is about 44,000 ppm by weight.

3. The method of claim 2 wherein the amount of surfactant is about 4000 ppm by weight and the amount of adhering agent is about 5000 ppm by weight.

4. A method for increasing the yield of fruit produced from soybean plants which comprises applying to the soybean plant environment during the flowering stage of the growth cycle an aqueous composition comprising from about 6 to below 18 ppm by weight active 2,4-D Herbicide, from about 10 to about 20,000 ppm by weight lower aliphatic alcohol, a surfactant and an adhering agent each in amounts of from about 10 to about 10,000 ppm.

5. The method of claim 4 wherein the amount of surfactant is about 400 ppm by weight and the amount of adhering agent is about 500 ppm by weight.

6. The method of claims 1 or 4 wherein the lower aliphatic alcohol is methanol, the surfactant is Tween 20, and the adhering agent is diesel fuel.

7. The method of claims 1 or 4 wherein the aqueous composition is applied to the soybean plant at a rate above about 0.3 gallons/acre.

8. A plant growth stimulant aqueous composition comprising from about 60 to 120 ppm by weight active 2,4-D Herbicide, from about 10,000 to about 80,000 ppm by weight lower aliphatic alcohol, a surfactant and an adhering agent each in amounts of from about 10 to about 10,000 ppm.

9. The composition of claim 8 wherein the amount of active 2,4-D Herbicide is about 100 ppm by weight and the amount of lower aliphatic alcohol is about 44,000 by weight.

10. The composition of claim 9 wherein the amount of surfactant is about 4000 ppm by weight and the amount of adhering agent is about 5000 ppm by weight.

11. A plant growth stimulant aqueous composition comprising from about 6 to below 18 ppm by weight active 2,4-D Herbicide, from about 10 to about 20,000 ppm by weight lower aliphatic alcohol, a surfactant and an adhering agent each in amounts of from about 10 to about 10,000 ppm.

12. The composition of claim 11 wherein the amount of surfactant is about 400 ppm by weight and the amount of adhering agent is about 500 ppm by weight.

13. The composition of claims 8 or 11 wherein the lower aliphatic alcohol is methanol, the surfactant is Tween 20, and the adhering agent is diesel fuel.

* * * * *

UNITED STATES PATENT AND TRADEMARK OFFICE
CERTIFICATE OF CORRECTION

PATENT NO. : 4,274,861
DATED : June 23, 1981
INVENTOR(S) : Alan Henderson et al.

It is certified that error appears in the above-identified patent and that said Letters Patent are hereby corrected as shown below:

In column 4, line 19, change "same data, that data" to

--same date, that date--.

In column 8, line 15, after "1. A method for increasing"

insert

--the yield of fruit produced from soybean plants which comprises applying to the soybean plant environment during the flowering--.

Signed and Sealed this

Eighth Day of September 1981

[SEAL]

Attest:

Attesting Officer

GERALD J. MOSSINGHOFF

Commissioner of Patents and Trademarks